(12) United States Patent
Ikonen et al.

(10) Patent No.: US 10,940,330 B2
(45) Date of Patent: Mar. 9, 2021

(54) DOSIMETRIC PROJECTION OF COLLIMATOR GEOMETRY

(71) Applicant: Varian Medical Systems International AG, Steinhausen (CH)

(72) Inventors: Timo Ikonen, Espoo (FI); Christopher Boylan, Helsinki (FI); Ari Harju, Espoo (FI); Petri Hiltunen, Espoo (FI); Juha Kauppinen, Espoo (FI); Petri Kokkonen, Helsinki (FI); Viljo Petaja, Espoo (FI); Marko T Rusanen, Espoo (FI); Sami P Siljamaki, Vantaa (FI); Tuomas E Torsti, Helsinki (FI); Esa Kuusela, Espoo (FI); Antti Karjalainen, Edinburgh (GB)

(73) Assignee: VARIAN MEDICAL SYSTEMS INTERNATIONAL AG, Steinhausen (CH)

(*) Notice: Subject to any disclaimer, the term of this patent is extended or adjusted under 35 U.S.C. 154(b) by 0 days.

(21) Appl. No.: 16/359,562

(22) Filed: Mar. 20, 2019

(65) Prior Publication Data

US 2020/0298018 A1 Sep. 24, 2020

(51) Int. Cl.
*A61N 5/10* (2006.01)
*G16H 20/40* (2018.01)

(52) U.S. Cl.
CPC ......... *A61N 5/1031* (2013.01); *A61N 5/1001* (2013.01); *A61N 5/1045* (2013.01); *A61N 5/1077* (2013.01); *A61N 5/1048* (2013.01); *G16H 20/40* (2018.01)

(58) Field of Classification Search
CPC .. A61N 5/1031; A61N 5/1001; A61N 5/1045; A61N 5/1077; A61N 5/1048; G16H 20/40
USPC .......................................................... 378/65
See application file for complete search history.

(56) References Cited

U.S. PATENT DOCUMENTS

2018/0104511 A1 4/2018 Hsu et al.

OTHER PUBLICATIONS

Varian Medical Systems, Fluence Delivery with Smart LMC Algorithm, Eclipse Algorithms Reference Guide, Mar. 2010, pp. 319-321.

(Continued)

*Primary Examiner* — Courtney D Thomas
(74) *Attorney, Agent, or Firm* — Varian IP Legal (57) ABSTRACT

A method of calculating radiation dose includes dosimetric projection of a collimator geometry. The method includes defining a three-dimensional (3D) geometry of a collimating device which defines an aperture configured to allow a radiation beam passing through, projecting the collimating device along the radiation beam into a two-dimensional (2D) geometry in a plane, calculating dosimetric opacity values of the collimating device at locations adjacent to the aperture based on the 3D geometry of the collimating device, and calculating transport of the radiation beam through the collimating device based on the 2D geometry projected in the plane and using the dosimetric opacity values of the collimating device at the locations adjacent to the aperture.

20 Claims, 9 Drawing Sheets

(56) References Cited

OTHER PUBLICATIONS

PCT, International Search Report and Written Opinion of the International Searching Authority in PCT/IB2020/051444, Apr. 30, 2020, 11 pages.
Arnfield et al., "A method for determining multileaf collimator transmission and scatter for dynamic intensity modulated radiotherapy," Med. Phys., 27 (10), Oct. 2000, pp. 2231-2241.
Hardcastle et al., "Note: Multileaf collimator end leaf leakage: implications for wide-field IMRT," Phys. Med. Biol., 52 (21), Nov. 2007, pp. N493-N504.

DOSIMETRIC PROJECTION OF COLLIMATOR GEOMETRY

TECHNICAL FIELD

This application relates generally to radiation methods and apparatuses. In particular, various embodiments of methods of dosimetric projection of collimator geometry and calculation of dose deposition for treatment planning are described.

BACKGROUND

External beam radiotherapy requires treatment planning to determine a desired radiation dose to the target and a maximal dose which can be safely absorbed by healthy tissue or organs within the treatment volume near the target. In treatment planning, dose deposited within a treatment volume is calculated or predicted using a suitable dose calculation algorithm, which may involve tracking of the radiation beam from the source to the treatment volume.

To achieve a desirable dose distribution in the target, collimating devices are used in a treatment machine to size, shape and/or modulate the intensity of the beam. For example, multileaf collimators (MLCs) are widely used in radiotherapy machines to support various forms of treatment, including 3D conformal radiation therapy (3D-CRT), intensity-modulated radiotherapy (IMRT), volumetric modulated arc therapy (VMAT), stereotactic radiosurgery (SRS), and so on. An MLC includes a plurality of pairs of beam-blocking leaves which can be independently moved in and out of a radiation beam. In use, a number of selected beam-blocking leaves are positioned in the radiation beam forming an aperture through which the unblocked beam passes. The shape and size of the aperture in the MLC define a shaped field at the target in the isocenter plane. In some applications, the aperture in an MLC is configured sufficiently small for small-field radiotherapy or stereotactic radiosurgery (SRS). Alternatively, SRS cones may be used to perform stereotactic radiosurgery. An SRS cone is a collimating device typically made from tungsten having a small conical hole to allow a radiation beam passing through for focused beam delivery.

As a radiation beam from a source passes through an MLC, SRS cone, and/or other collimating devices, the characteristics of the beam, including the shape or fluence of the beam, are modified and thus need be determined to provide input for a dose calculation algorithm to compute or predict the dose deposited in the treatment volume. One conventional approach of calculating the shape or fluence of a beam exiting a collimating device such as an MLC is to project the MLC geometry along the beam line onto a plane, essentially flattening the three-dimensional (3D) MLC geometry into a two-dimensional (2D) opening, where the structural details of the MLC leaf tips are not taken into account in the calculation. While this approach is suitable in many cases, it becomes less accurate in planning small-field radiotherapy including stereotactic radiotherapy where the size of the treatment field is comparable to the size of the 3D structural features of the MLC leaf tips. In small-field radiotherapy, the 3D geometry details of an MLC have to be taken into account to accurately predict dose distributions for small fields. However, fully 3D models for beam tracking or fluence calculation are currently prohibitively expensive and computationally too slow to be used in a treatment planning system in a clinical environment.

Therefore, there is a need for methods of beam tracking and dose calculation that can provide both accuracy and speed for treatment planning of radiation therapy. There is a particular need for such methods for planning small-field radiotherapy using a radiation system including an multileaf collimator.

BRIEF SUMMARY

Embodiments of this disclosure provide for a method of tracking or calculating beam fluence passing through a collimating device. The three-dimensional (3D) shape of the collimating device, such as an MLC, is taken into account by a local dosimetric projection of the geometry. For example, the dimension of an MLC part along the beam is projected into a dosimetric opacity value or dosimetric thickness. The dosimetric projection is based on the realistic 3D geometry of the MLC, but an algorithm can be made faster than a full 3D model by making the dosimetric projection local (e.g., around the MLC leaf tip and edges) and by defining bounding points or surfaces. The dosimetric opacity can be calculated at the geometrical boundaries by e.g. ray-tracing or analytical calculation, and by interpolating between them or using analytical approximations. The dependence on variables such as collimator shape and position can be taken into account by, e.g., parameterizing the dosimetric projection as a function of the variable or by solving the dependence by analytical approximation. The dosimetrically projected opacity values or thicknesses can be then used as input in a dose calculation algorithm within a fluence calculation module. The disclosed method requires a computational effort comparable to the current 2D approach, but improves the accuracy of dose calculation significantly to a level comparable to a full 3D model.

In one embodiment, a method comprises the steps of defining a 3D geometry of a collimating device which defines an aperture configured to allow a radiation beam passing through, projecting the collimating device along the radiation beam into a 2D geometry in a plane, calculating dosimetric opacity values of the collimating device at locations adjacent to the aperture based on the 3D geometry of the collimating device, and calculating transport of the radiation beam through the collimating device based on the 2D geometry projected in the plane and using the dosimetric opacity values of the collimating device at the locations adjacent to the aperture.

In another embodiment, a computer product comprises a non-transitory computer-readable medium storing instructions executable by a computer system. The instructions comprises defining a 3D geometry of a collimating device which defines an aperture configured to allow a radiation beam passing through, projecting the collimating device along the radiation beam into a 2D geometry in a plane, calculating dosimetric opacity values of the collimating device at locations adjacent to the aperture based on the 3D geometry of the collimating device, and calculating transport of the radiation beam through the collimating device based on the 2D geometry projected in the plane and using the dosimetric opacity values of the collimating device at the locations adjacent to the aperture.

In a further embodiment, a computer system comprises a processor and memory storing instructions executable by the processor. The instructions comprises defining a 3D geometry of a collimating device which defines an aperture configured to allow a radiation beam passing through, projecting the collimating device along the radiation beam into a 2D geometry in a plane, calculating dosimetric opacity values of the collimating device at locations adjacent to the aperture based on the 3D geometry of the collimating device, and calculating transport of the radiation beam through the collimating device based on the 2D geometry projected in the plane and using the dosimetric opacity values of the collimating device at the locations adjacent to the aperture.

This Brief Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF EMBODIMENTS

Referring to FIGS. 1-11, various embodiments of dosimetric projection of a collimator geometry and dose calculation methods will now be described.

Figure 1:
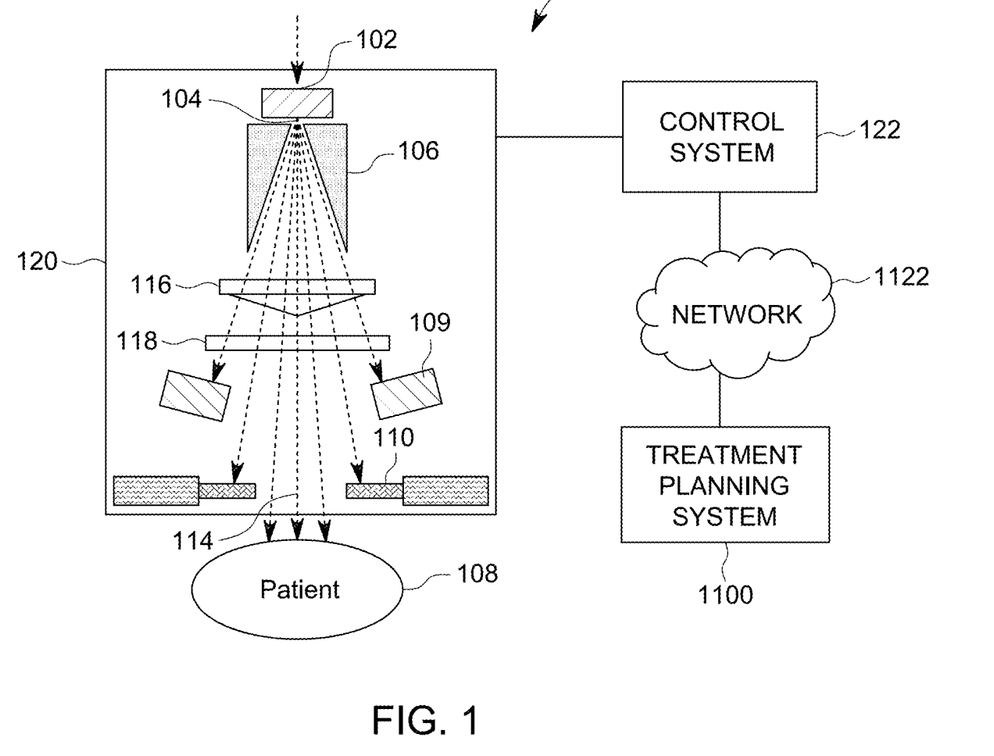
FIG. 1 is a simplified illustration of a radiation system according to embodiments of this disclosure.

FIG. 1 is a simplified illustration of a radiation system 100 in which the methods of the disclosure can be implemented. As shown, the radiation system 100 may include a radiation source 102 producing or emitting a beam 104 of radiation such as photons, electrons, protons, or other types of radiation. For example, the radiation source 102 may include a metallic target configured to produce a beam of x-rays or photons upon impingement of electrons. It should be noted that while various embodiments are described in conjunction with an x-ray system, the principle of dosimetric projection of a collimator geometry and dose calculation method described in this disclosure can also be practiced in other types of radiation system such as ion, electron, carbon, or proton systems.

The radiation system 100 may include various collimating devices or components configured to modify the size, shape, fluence, and other characteristics of the beam. By way of non-limiting example, a primary collimator 106 adjacent to the source 102 generally limits the extent of the beam 104 as it travels away from the source 102 toward a subject such as a patient 108. Optionally, motorized secondary collimators or collimation jaws 109 may be included to define the field size. A multileaf collimator (MLC) 110 may be disposed between the source 102 and the patient 108 to shape the beam, as indicated by the shaped field 112 shown in FIG. 1A. The MLC 110 may be rotated about the central beamline or axis 114, placing the MLC 110 in various orientations. The radiation system 100 may optionally include a flattening filter 116 to provide a uniform beam profile. Alternatively, the radiation system does not include any flattening filter or is flattening-filter-free (FFF) to enhance dose rates for treatment. Ion chamber 118 monitors the parameters of the beam from the source 102.

The source 102, primary collimator 106, secondary collimators 109, MLC 110, and other devices or components may be enclosed in the treatment head 120, which can be rotated by a gantry (not shown) about an axis such as a horizontal axis. Thus, the system 100 can deliver radiation to a target in the subject 108 from various beam angles. The shape, size, and/or intensity of the beam 104 can be adjusted or dynamically adjusted by the MLC 110 as the beam angle is stepped or swept around the target. The operation of the source 102, MLC 110, and other devices of the radiation system 100 can be controlled by a control system 122. The control system 122 may comprise a computer processor which receives and executes a treatment plan generated by a treatment planning system 1100 to be described in greater detail below.

Figure 1A:
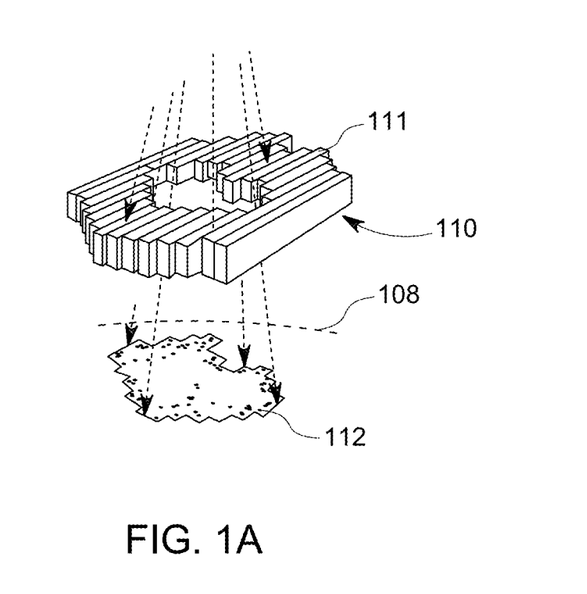
FIG. 1A is an enlarged perspective view of the multileaf collimator (MLC) shown in FIG. 1.

The MLC 110 may be a single level MLC as shown in FIGS. 1 and 1A or a multi-level MLC. As used herein, the term "MLC" or "multileaf collimator" refers to a collection of a plurality of beam-blocking leaves 111 each of which can be longitudinally moved in and out of a beam to modify one or more parameters of the beam such as the beam shape, size, energy, or fluence etc. Each beam-blocking leaf 111 may be driven by a motor with a lead screw or other suitable means. The beam-blocking leaves 111 may be arranged in pairs. The beam-blocking leaves of each pair may be brought in contact or retracted from each other to close or open a path for a radiation beam to pass through the MLC. The beam-blocking leaves may be arranged in opposing banks and supported by a frame, box, carriage or other support structure, which has features allowing the individual beam-blocking leaves to extend into and retract from the beam. The frame, box, carriage or other support structure can be further moved or translated in addition to the individual leaf travel.

The beam-blocking leaves 111 may have various leaf tip profiles or end portion configurations, and leaf edge profiles or leaf side configurations. By way of non-limiting example, the beam-blocking leaves 111 of the MLC 110 may have a flat front-end surface and a flat side surface. In both a side view and a top view, a beam-blocking leaf with a flat front-end surface may be shown to have a straight line orthogonal to the leaf longitudinal moving direction and two right angles at each side of the straight line. As used herein the term "top view" refers to a view observed from the source or in a direction along the central beamline. In some embodiments, the beam-blocking leaves of the MLC 110 may have a curved front-end surface. In a side view, a beam-blocking leaf with a curved front-end surface may be shown to have a curved line with a radius and two parallel lines at either side of the curved line. In a top view, a leaf with a curved front-end surface may be shown to have a straight line orthogonal to the leaf longitudinal moving direction and two right angles on each side of the straight line. In the Detail Description and appended Claims, the term "square shape" may be used to describe a leaf tip profile which, in a top view, has a straight line orthogonal to the leaf longitudinal moving direction and two right angles at each side of the straight line. The term "non-square shape" may be used to describe any leaf tip profile which, in a top view, does not have a square shape. The non-square shape in a top view may include a curved or elliptic shape or a shape of a chamfer leaf as will be described in greater detail below.

In some embodiments, the MLC leaf tip may have a circular or non-circular profile. In some embodiments, the MLC leaf side may have a tongue-and-groove feature, a tilted surface, or some other type of profile.

In some embodiments, the beam-blocking leaves 111 of the MLC 110 may have a tip profile that includes a combination of a curved surface portion and a beveled or flat surface portion at each side of the curved surface portion. The term "chamfer leaf" may be used herein to refer to a leaf which includes a combination of a curved end surface portion and beveled or flat end surface portions at either side of the curved end surface portion. In a top view or beam's eye view, the end portion or tip of a chamfer leaf may be shown to have a straight middle line section orthogonal to the leaf longitudinal moving direction and beveled or angled lines sections at each side of the straight middle line section.

In some embodiments, the MLC 110 may be a multi-level MLC. By way of example, the MLC 110 may include a first MLC in a first level distal to the source 102 and a second MLC in a second level proximal to the source 102. The the first and second MLCs may be arranged such that the moving direction of individual beam-blocking leaves of the first and second MLCs are generally in parallel. Alternatively, the first and second MLCs may be arranged such that the moving direction of the beam-blocking leaves of the first MLC is non-parallel e.g. perpendicular to the moving direction of the beam-blocking leaves of the second MLC. The first and second MLCs may be arranged such that the leaves of the second MLC may laterally offset the leaves of the first MLC in a top view or as viewed in a direction from the source.

In some embodiments of this disclosure, the MLC may be absent or combined with other collimating or beam shaping devices, including, but not limited to, collimation jaws, cones, wedges, and filters.

In operation, the MLC 110 may be configured to form an aperture defining a shaped field 112 approximating the target geometry at the isocenter plane. Alternatively, the MLC 110 may be configured to define differently shaped fields at different MLC orentations and/or beam angles, and the doses of multiple fields may be summed to build up a desired dose distribution in the target. Radiation may be delivered intermittently or statically wherein the MLC leaves are in positions while radiation is being delivered. Radiation may also be delivered dynamically wherein the MLC leaves are moving or the MLC is rotating while radiation is being delivered. In some applications, the aperture of the MLC is formed substantially small for small-field radiotherapy such as stereotactic radiosurgery (SRS). By way of non-limiting example, the MLC may be configured to form an aperture defining a field size ranging from 1 to 10 millimeters, or from 4 to 5 millimeters. A field size of 1 to 10 millimeters may be comparable to the projected dimensions of MLC leaf tips, which may have a curved profile in a side view or a non-square profile in a top view as described above.

In treatment planning for radiation delivery, dose deposited within the target or treatment volume is calculated or predicted using a suitable dose calculation algorithm. To accurately calculate dose deposition, various factors are considered including the composition of tissue and characteristics of the radiation beam from the source. As the radiation beam produced by the source transports through various collimating devices including e.g. an MLC, the characteristics of the beam exiting the MLC need be determined and provided to the dose calculation algorithm for computing or predicting dose deposited in the target or treatment volume.

Figure 2:
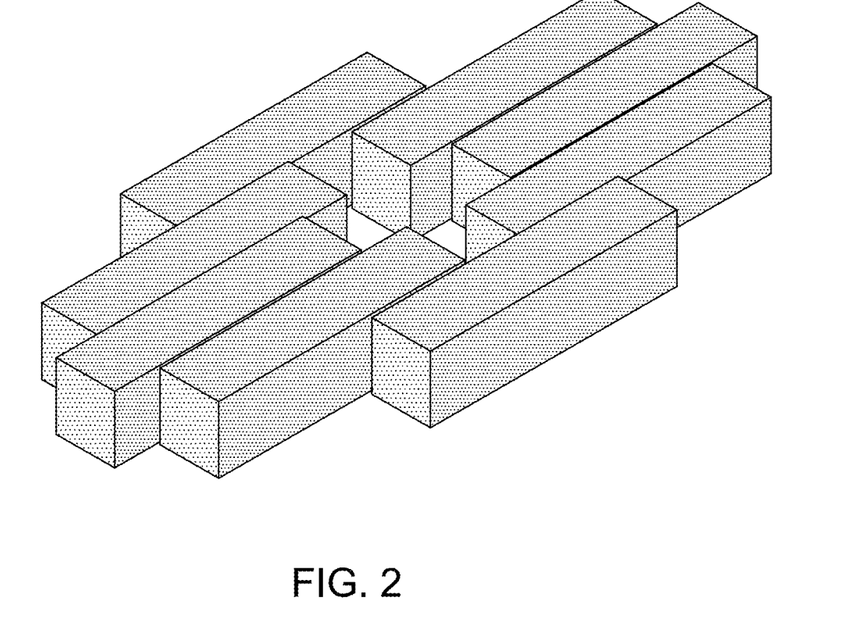
FIG. 2 illustrates a three-dimensional (3D) model for calculating beam transport through an MLC.

FIG. 2 illustrates a method or model for calculating radiation transport through a collimating device such as an MLC. According to the method shown in FIG. 2, a 3D collimator geometry model is constructed and computer software based on the 3D model created. The 3D model for calculating radiation transport can be very accurate because the structural details of the 3D collimator geometry, including the fine features in the region near the aperture, are taken into account in calculation. However, constructing a 3D model and computer software based on the 3D model in full detail are extremely time-consuming. Calculation of radiation transport based on a fully 3D model is computationally too slow to be used in a treatment planning system in a clinical environment, especially in treatment plan optimization.

Figure 3:
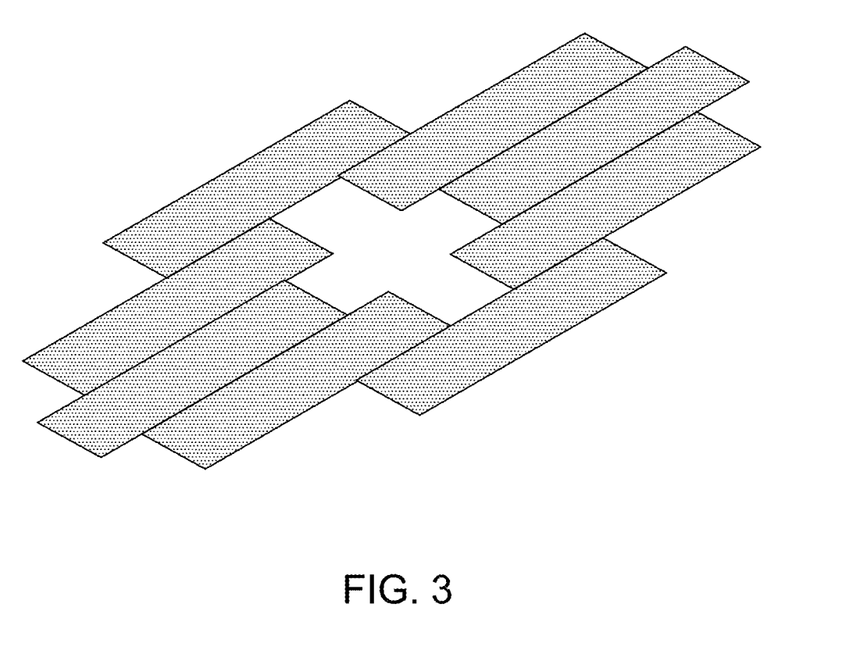
FIG. 3 illustrates a two-dimensional (2D) model for calculating beam fluence through an MLC.

FIG. 3 illustrates another method or model for calculating radiation transport through a collimating device such as an MLC. According to the method shown in FIG. 3, a 3D collimator geometry is flattened or projected along the beam line into a 2D geometry and computer software based on the 2D geometry is created. The 2D model for calculating radiation transport is fast and suitable for many clinical cases. However, conventional 2D models for calculating radiation transport are less accurate, especially around the edges of the aperture because the fine features of the aperture edges are not modeled accurately, which is especially relevant when the aperture is small for e.g. stereotactic radiosurgery. For instance, an actual MLC leaf end portion having a curve profile in a side view may be shown as having a square shape when the MLC leaf is flattened or projected along the beamline into a 2D geometry. As such, the fine features of the actual MLC leaf tip profile, which would affect attenuation or transmission of the radiation beam, are not taken into account in conventional 2D modeling. Likewise, the fine features of chamfer leaves described above are not taken into account in conventional 2D modeling for calculating radiation transport. In small-field radiotherapy especially stereotactic radiotherapy, the field size may be comparable to the projected dimension of the MLC leaf tip profile. Therefore, the fine features of the aperture edges have to be taken into account to accurately calculate radiation transport.

Figure 4:
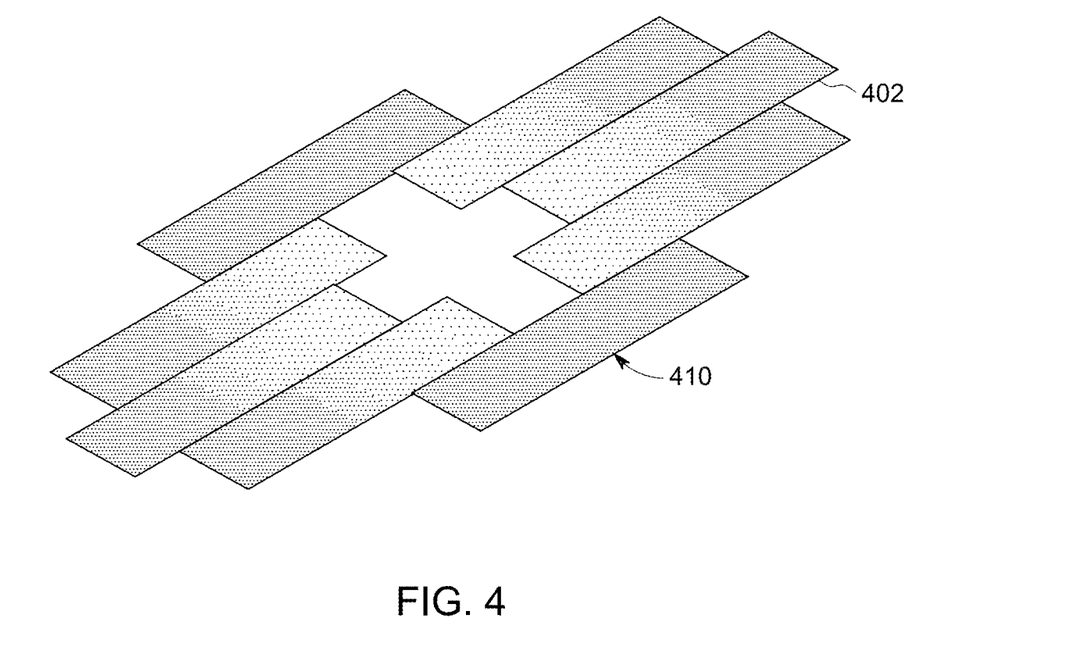
FIGS. 4 and 5 illustrate a dosimetric projection model for calculating beam fluence through an MLC according to embodiments of the disclosure.

FIG. 4 illustrates a new method or model for calculating radiation transport through a collimating device 410 according to embodiments of the disclosure. According to the disclosed method, the geometry of the collimator 410 is flattened or projected along the beam line from 3D to 2D on a plane, and a calculation algorithm is created based on the 2D geometry. While the collimator geometry is flattened from 3D to 2D, dosimetric opacity values or dosimetric thicknesses of the collimator parts are calculated based on the actual 3D geometry of the collimator. The dosimetric opacity values or thicknesses can be encoded in the calculation algorithm based on the 2D geometry, as schematically shown in a range of shades around the edges of the aperture in FIG. 4. Because the calculation algorithm model is in 2D, the computation is fast. Further, because the dosimetric opacity values or thicknesses are obtained based on the actual 3D shape of the collimator, the calculation of radiation transport, including the calculation at the edges of the aperture, is as accurate or almost as accurate as the 3D model.

Figure 5:
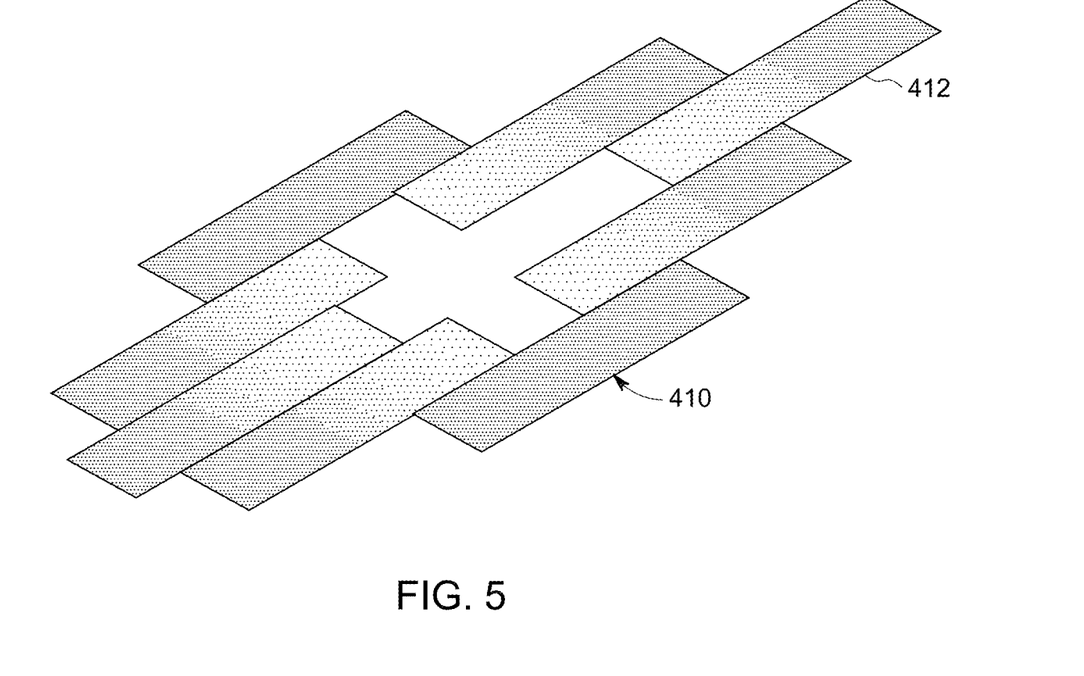

FIG. 5 shows that the dosimetric opacity values or thicknesses depend on both the 3D shape of the collimator parts (e.g. MLC leaf tip profiles) and the positions of the collimator parts within the radiation field. For example, a beam-blocking leaf 412 of the MLC 410 at a position shown in FIG. 5 exhibits a broader range of shades than does the same leaf 412 at a different position shown in FIG. 4. This can be explained as that the dosimetric opacity value or thickness is a function of the length or dimension of the collimator part along the beam path. For ease of description of various embodiments, the term "dosimetric projection" may be used hereafter to refer to a method of obtaining a dosimetric opacity value or thickness of a collimator based on the 3D shape or geometry of the collimator.

Figure 6:
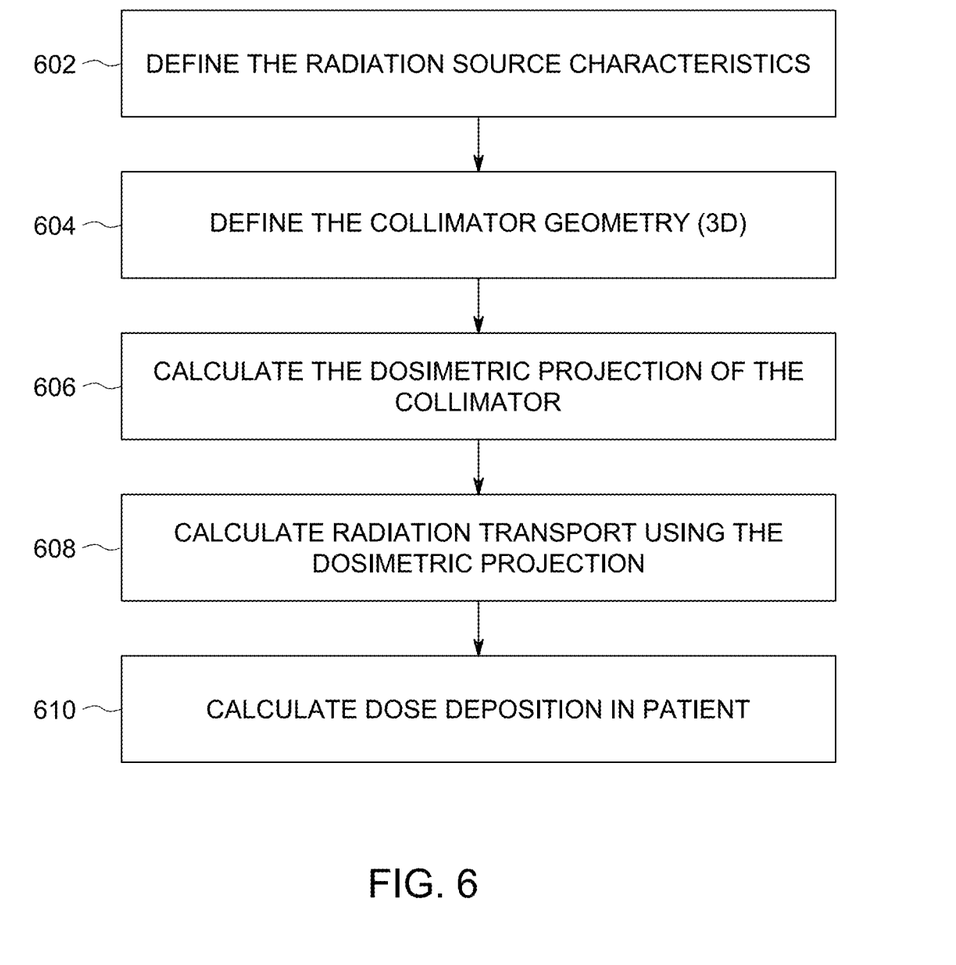
FIG. 6 is a flowchart illustrating a method of calculating dose deposition using dosimetric projection of a collimator geometry according to embodiments of the disclosure.

FIG. 6 illustrates a method of dose calculation using dosimetric projection of a collimator geometry according to embodiments of the disclosure. The method can be implemented for planning radiation delivery with a radiation system 100 shown in FIG. 1 or other suitable radiotherapy machines. The method can be performed in a treatment planning system 1100 shown in FIG. 11 to be described in greater detail below. The method may start at block 602 by defining the radiation source characteristics. Various methods can be used to define the radiation source characteristics including Monte Carlo simulation and empirical measurements. These methods are generally known in the art and therefore their detailed description is omitted herein to focus on the description of various embodiments of this disclosure. In general, based on the design of a radiation machine including the target and electron beam energy, the fluence and energy of the radiation produced by the source and direction at all points in a reference plane can be calculated. The characteristics of the radiation source can be provided as an initial spatial photon spectrum describing the fluence, energy and directions in a beam reference plane.

At block 604, the geometry of the collimator is defined. As used herein, the term "collimator" refers to any collimating device configured to modify one or more characteristics of radiation from the source, including but not limited to, multileaf collimators (MLCs), stereotactic radiosurgery (SRS) cones, motorized collimation jaws, custom-molded or machined collimation blocks, and any other collimating devices which may be included in a radiation machine. As used herein, the term "geometry of a collimator" refers to the geometry including the contour which defines an aperture of the collimator allowing radiation passing through. The geometry of the collimator defining the aperture has a three-dimensional configuration, wherein the shapes in cross-sections traverse the dimension along the beamline may or may not vary. The 3D geometry of a collimator may be predetermined by the design of the collimator such as in the case of a custom-molded collimation block, which may in turn be dictated by the geometry of the target to be treated.

In the case of a multileaf collimator, the 3D geometry of the MLC may be determined by the positioning of a set of beam-blocking leaves, which may readily change depending on the treatment plan. As described above, the beam-blocking leaves of an MLC may have various leaf tip profiles e.g. curved or rounded leaf end surfaces, whose beam's eye view or beam-blocking effect may change depending on the positions of the beam-blocking leaves. Further, as an MLC may rotate about the central beam line, a same geometry of the MLC may have different collimating or attenuation effect especially at the edges of the aperture when the MLC is in different orientations because the tips of the beam-blocking leaves defining the aperture change the angles with respect to the source. The 3D geometry of the MLC may be defined by specifying the spatial positions of the beam-blocking leaves and their angles with respect to the central beamline, the physical dimensions, and the leaf tip profiles of the beam-blocking leaves, and other variables.

At block 606, dosimetric projection of the collimator is calculated. Dosimetric projection of a collimator involves in projection of the collimator geometry from 3D to 2D along the beamline wherein the dimension of the collimator along the beamline is represented or encoded with a dosimetric opacity value. As used herein, the term "dosimetric opacity" refers to a quality of the collimator in attenuating radiation. The value of dosimetric opacity is obtained by applying the dosimetric projection method on the given collimator. The value of dosimetric opacity depends on the material the collimator is made of, the physical dimension of the collimator or the "thickness" of the material along which the radiation passes, and the position of the collimator in relation to the beam centerline. Therefore, term "dosimetric opacity" may be used interchangeably with the term "dosimetric thickness." The dosimetric opacity value of a given collimator part can be calculated using a suitable method based on the realistic 3D geometry of the collimator.

According to embodiments of the disclosure, local dosimetric projection of the collimator geometry is performed. In a local dosimetric projection, dosimetric opacity values at locations adjacent to the aperture defined by the collimator are calculated. By way of non-limiting example, a plurality of points or surfaces on an MLC leaf end portion, which collectively may represent a boundary of the MLC leaf end or indicate the leaf tip profile, are specified. The dosimetric opacity values at these bounding points or surfaces may be calculated by for example ray-tracing or any other suitable analytical methods. Interpolating of dosimetric opacity values between the bounding points and surfaces or analytical approximation may be performed.

Figure 7:
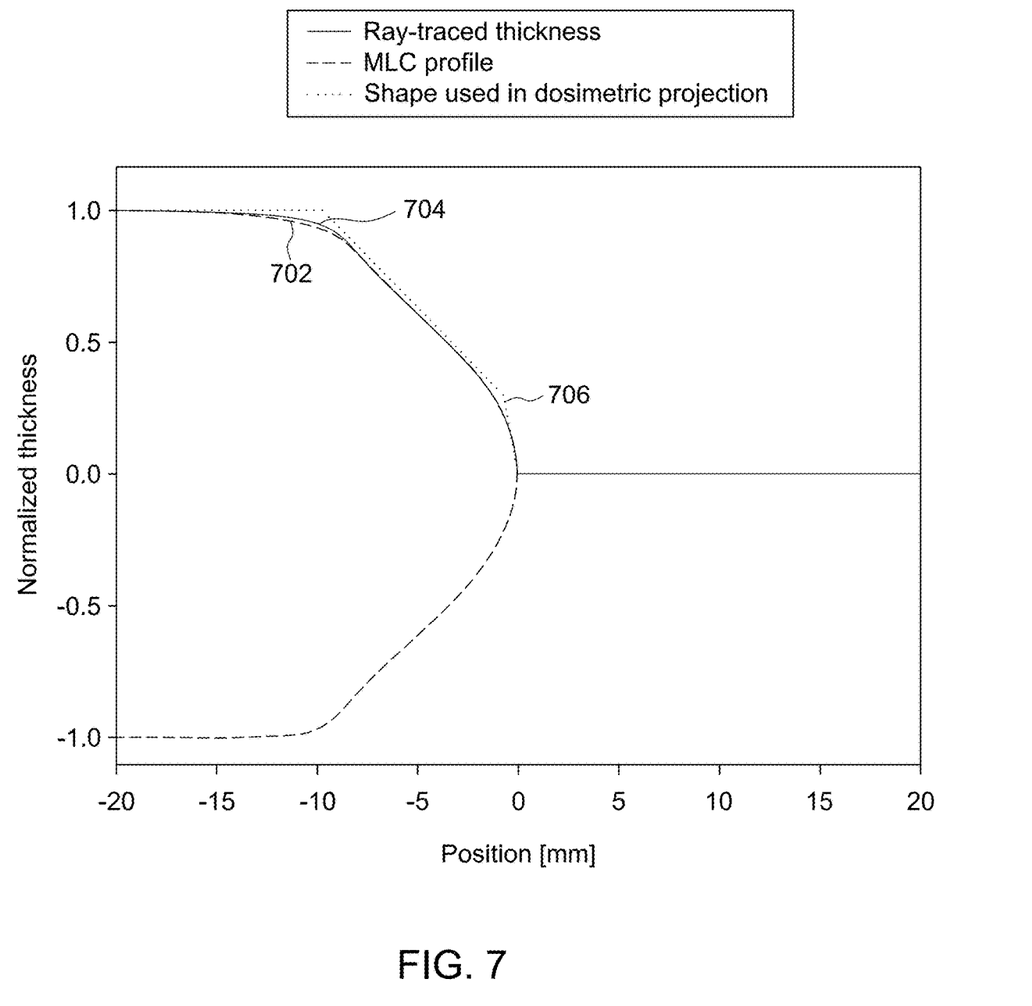
FIG. 7 illustrates an example method of calculating dosimetric opacity values for an MLC leaf according to embodiments of the disclosure.

FIG. 7 illustrates an example collimator part (an MLC beam-blocking leaf) and a method of calculating dosimetric opacity values according to embodiments of the disclosure. In FIG. 7, the horizontal axis indicates leaf projection positions and the vertical axis represents normalized leaf thicknesses. Curve 702 depicts the physical geometry or real profile of the collimator part at a position relative to the source. As shown, the example MLC leaf has a curved leaf tip profile. The dots on the curve 702 may represent specified bounding points or surfaces for calculating dosimetric opacity values. Curve 704 shows a calculated thickness of the collimator part. As shown, curve 704 substantially superimposes over curve 702, indicating that the thickness of the collimator part can be accurately calculated using an analytical or numerical method such as ray-tracing and interpolating known in the art. Based on the results of ray-tracing, the dosimetrically projected thickness can be defined, for example, as a function approximating the raytraced curve 704. The dosimetric projection can be defined in such a way that the approximation remains valid and takes into account the dependence of the dosimetric thickness on the position of the MLC leaf, as indicated by the illustrations in FIG. 4 and FIG. 5. In FIG. 7, the dosimetrically projected shape or thickness is indicated by curve 706.

Figure 8:
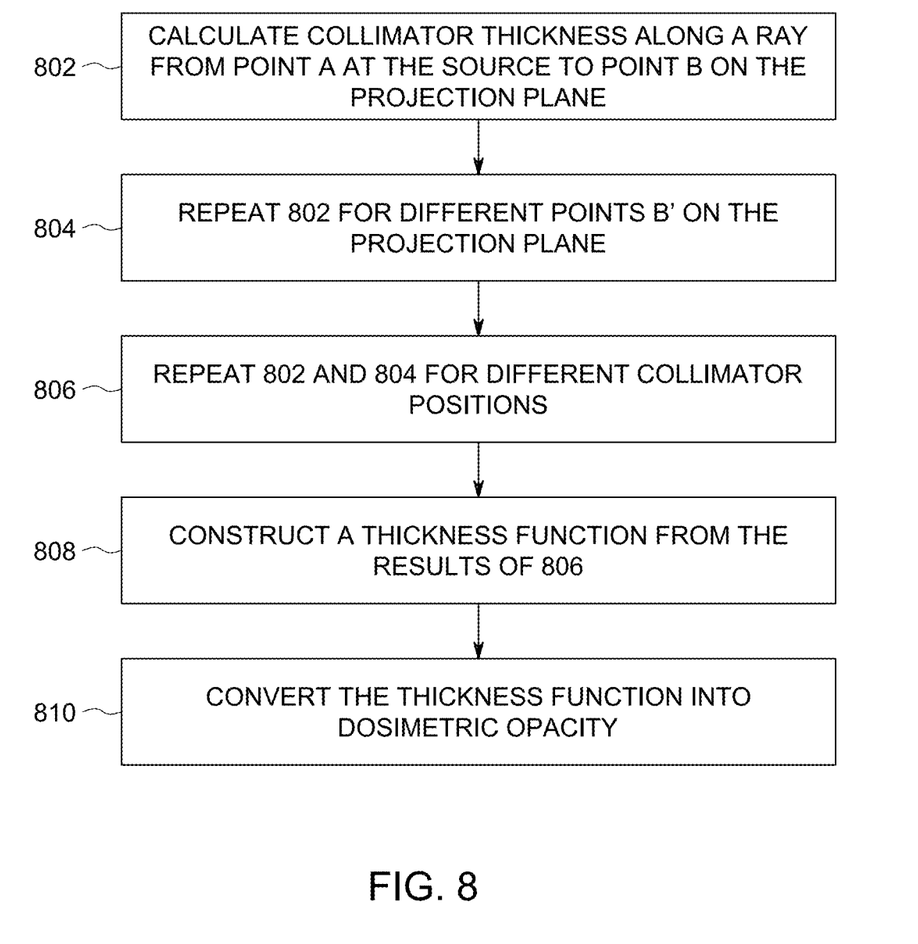
FIG. 8 is a flowchart illustrating example steps of dosimetric projection of a collimator geometry according to embodiments of the disclosure.

FIG. 8 is a flowchart illustrating example steps for calculating dosimetric projection of a collimator. At 802, the collimator thickness along a ray from point A at the source to point B on the projection plane is calculated. The calculation of collimator thickness can be conducted numerically e.g. by ray-tracing or analytically. Analytical calculation can be conducted wherein the collimator is represented by a set of suitable geometric primitives, e.g., circles and lines in two dimensions or cylinders and planes in three dimensions. In calculation of the collimator thickness at 802, the collimator position can be fixed.

At 804, the calculation of 802 is repeated for different points B' on the projection plane. The different points B' can be those located adjacent to the aperture defined by the collimator.

At 806, the calculation of 804 is repeated for different positions of the collimator.

At 808, a thickness function from the results of 806 is constructed. This can be done by e.g. interpolating between the points calculated at 806 or by an analytical approximation. The function based on interpolation can take the form of a pre-calculated look-up table coupled with an interpolation algorithm such as multilinear interpolation or other suitable method known in the art. The function based on analytical approximation can be obtained, e.g., by numerically fitting an analytical function such as a multidimensional polynomial to the points calculated at 806. The analytical approximation can also be obtained from the exact analytical solution, if such is available, by approximating the solution for greater numerical efficiency by using numerical computation methods known in the art.

At 810, the thickness function is converted into dosimetric opacity. The radiation source characteristics such as the primarily particle type and energy spectrum and radiation transport physics can be considered in obtaining the opacity. This step may be implementation dependent—it can be considered to be part of the radiation transport calculation (608 in FIG. 6) if the algorithm for radiation transport uses geometrical data (thickness) instead of transmission/opacity for the collimator components.

Figure 9:
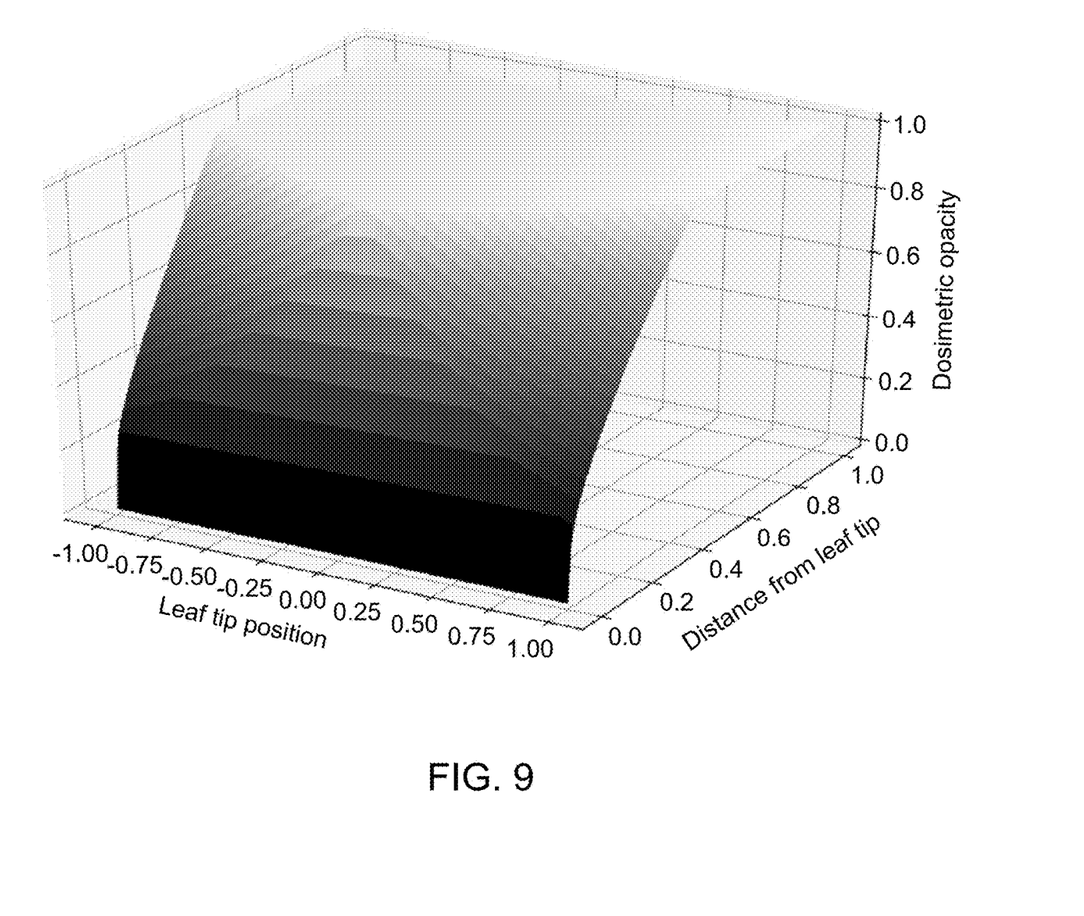
FIG. 9 is an image showing a result of dosimetric projection of an example collimator according to embodiments of the disclosure.

FIG. 9 is an image showing a result of dosimetric projection, the dosimetric opacity using a single MLC leaf as an example. In FIG. 9, the vertical axis indicates dosimetric opacity value, and the horizontal axes indicate the leaf tip poistion and the distance from the leaf tip respectively. The units of the axes in FIG. 9 are arbitrary for illustration purpose. FIG. 9 shows that for an exemplary MLC leaf, the dosimetric opacity can be represented by a function of two variables, the leaf position and distance from the leaf tip.

Returning to FIG. 6, at block 608, the method may proceed to calculate radiation transport using the dosimetric opacity values or thicknesses. Various algorithms have been developed to calculate beam transport through collimating devices. These methods are generally known in the art and therefore their detailed description is omitted to avoid obscuring the description of various embodiments of this disclosure. In general, an algorithm for calculating radiation transport takes into account factors including primary source, extra focal source, electron contamination, photon scattering etc. According to embodiments of the disclosure, the dosimetric opacity values obtained by local dosimetric projection described above are used as input for an algorithm based on a 2D geometry model to calculate radiation transport. The beam exiting the collimator can be provided as a spatial fluence spectrum in a reference plane.

At block 610, the method may proceed to calculate dose deposition in the target within the treatment volume using a treatment planning software including a dose calculation algorithm. By way of non-limiting example, a method and algorithm based on pencil beam convolution-superposition may be used. Other suitable methods and algorithms based on e.g. Boltzmann transport equation (BTE) can also be used. It should be noted that the present disclosure is not limited to a particular dose calculation algorithm. Examples of commercially available dose calculation software include Acuros® XB dose calculation algorithm and the Anisotropic Analytical Algorithm (AAA), both available from Varian Medical Systems, Inc. of Palo Alto, Calif. As input for dose calculation, the spatial fluence spectrum that has been calculated in block 608 using the dosimetric opacity values or thicknesses at the boundary of the collimator defining the aperture are provided to the dose calculation algorithm.

Embodiments of this disclosure provide for an improved method of calculating radiation transport or transmission through a collimator using a 2D or quasi-2D model to achieve a calculation accuracy that approximates a 3D model. However, the disclosed method does not require calculation of radiation transmission in 3D geometry every time the result is needed or over the whole spatial extent of the collimator. Instead, the disclosed method may use dosimetric projection described above, to pre-calculate radiation transmission just once in 3D or in an approximate 3D geometry, pre-calculate only locally around the aperture defined by the collimator, and pre-calculate for different collimator positions (field sizes). Using the pre-calculated values, a 2D or quasi-2D geometry or computational model, algorithm, function, etc. that represents the radiation transport in a 3D geometry can be constructed by approximating the 3D details with a dosimetric opacity. The 2D or quasi-2D model of the dosimetric opacity can be implemented into the fluence calculation module of the treatment planning software in calculation of dose desposition.

Figure 10:
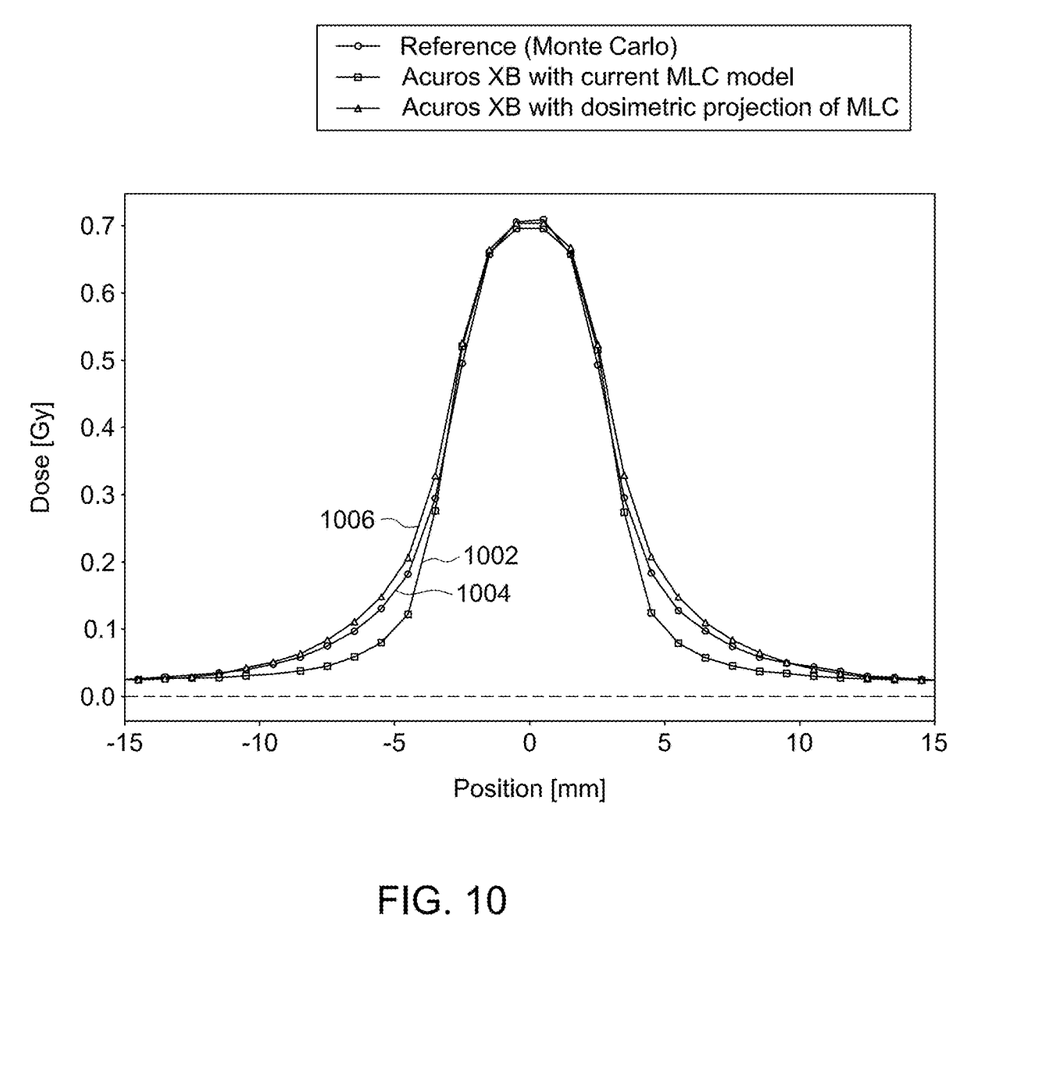
FIG. 10 shows plots comparing the accuracies of dose calculation based on various models.

FIG. 10 provides a comparison of accuracies of dose calculation using different methods. The plots shown in FIG. 10 depict dose distribution for a small field (e.g. 5×5 millimeters). Plots 1002 and 1004 show dose distributions calculated with Eclipse® treatment planning software and Acuros® XB dose deposition algorithm, with plot 1002 being calculated using a conventional 2D MLC modeling and plot 1004 being calculated using the dosimetric projection method according to embodiments of the disclosure. For comparison, plot 1006 shows a dose distribution calculated with Geant4 Monte Carlo using a full 3D MLC modeling. The results show that with the dosimetric projection method described herein, the dose deposition was more accurately calculated (plot 1004) than with the conventional 2D MLC modeling method (plot 1002), especially at the field edges (at +5 or −5 millimeters), as compared with the reference plot 806.

Various embodiments of dosimetric projection of a collimator geometry and dose calculation methods are described in connection with FIGS. 1-10. It will be appreciated that more or fewer steps, actions, or processes may be incorporated into the methods without departing from the scope of the disclosure. No particular order is implied by the arrangement of blocks shown and described herein. It further will be appreciated that the methods described in conjunction with FIGS. 1-10 may be embodied in a computer-based treatment planning system which performs dosimetric projection and dose calculation methods according to this disclosure. The invention may be in the form of a computer product comprising a computer-readable medium storing or carrying instructions which, when executed by a computer processor, cause the computer processor to perform the methods described in the disclosure. The instructions may be implemented as software code to be executed by a processor using any suitable computer language such as, Java, C++ or Perl using, e.g. conventional or object-oriented techniques. The computer-readable medium may include any suitable medium that is capable of storing or encoding a sequence of instructions for execution by the computer processor and that causes the computer processor to perform any one of the methodologies of the present invention. The computer-readable medium shall accordingly include, but not be limited to, solid-state memories, optical and magnetic disks. Examples of computer-readable medium include volatile and nonvolatile, removable and non-removable media for storage of computer-readable instructions. By way of non-limiting example, the computer-readable medium includes random access memory (RAM), read only memory (ROM), electrically erasable programmable ROM (EEPROM) flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information. In some embodiments, the instructions or software program may be encoded and transmitted using carrier signals adapted for transmission via wired, optical, and/or wireless networks conforming to a variety of protocols, including the Internet. As such, a computer-readable medium may be created using a data signal encoded with such programs. A computer-readable medium encoded with the program code may be packaged with a compatible device or provided separately from other devices e.g. via Internet download. Further, any such computer-readable medium may reside on or within a computer product e.g. a hard drive, a CD, or an entire computer system.

Figure 11:
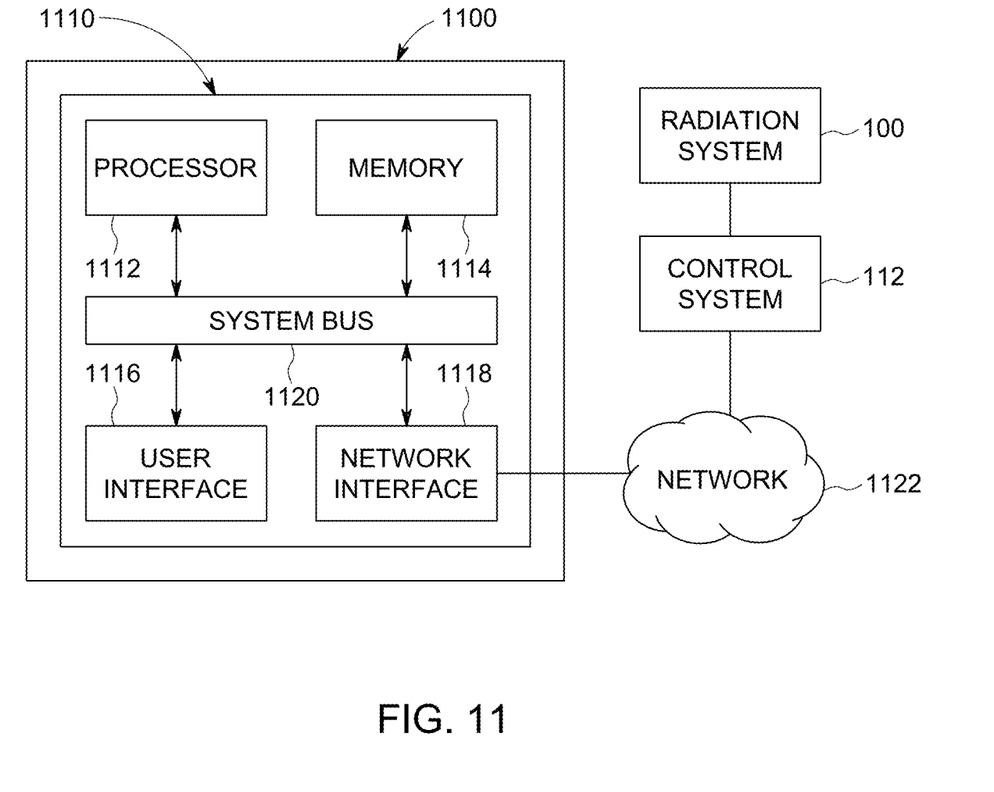
FIG. 11 is a simplified illustration of a computing system according to embodiments of the disclosure.

FIG. 11 schematically illustrates a treatment planning system 1100 upon which embodiments of the disclosure can be performed. The treatment planning system 1100 includes a computer system 1110, which generally comprises a processor 1112, memory 1114, a user interface 1116, and a network interface 1118, each of which is coupled to a system bus 1120.

The processor 1112 may include a central processing unit (CPU) that is generally known in the art, such as an INTEL® processor or an AMD® processor, or a graphical processing unit (GPU), such as an NVIDIA® GPU, or other type of processing unit. The processor 1112 may retrieve and execute computer-executable instructions from the memory 1114, which may cause the processor 1112 to perform any of the methods and/or steps according to the embodiments of this disclosure described above.

The memory 1114 may include any one of or a combination of volatile memory elements and nonvolatile memory elements. The memory 1114 may include a random-access memory (RAM) or other dynamic storage device for storing information and instructions to be executed by the processor 1112, and for storing temporary variables or other intermediate information during execution of instructions by the processor 1112. The memory 1114 may also include read-only memory (ROM) or other static storage device for storing static information and instructions for the processor 1112. The memory 1114 may further include a data storage device such as a magnetic disk or optical disk, for storing information and instructions. The memory 1114 (e.g. a non-transitory computer-readable medium) may comprise programs (logic) for operating the computer system and for performing applications including dosimetric projection and dose calculation as described above, or other treatment planning applications. In addition, the memory 1114 may include a database storing any information that can be selected by a user, such as a radiation oncologist or radiation therapist.

The user interface device 1116 may include components with which a user interacts with the computer system 1110, such as a keyboard, pointing device, pen, touch input device, voice input device, or the like. Output devices such as a display device, printer, speaker etc. may also be included in the computer system 1110.

The network interface 1118 allows the computer system to communicate with other devices or systems over a communication network 1122 such as the Internet or an intranet (e.g., a local area network). The network interface 1118 may include a Wi-Fi interface, Ethernet interface, Bluetooth interface, or other wireless or wired interfaces. The network interface 1118 allows the computer system 1110 to receive and send electrical, electromagnetic or optical signals that carry data streams representing various types of information. For instance, the network interface 1118 may allow the computer system 1110 to receive data streams representing software programs for treatment planning over the communication network 1122.

Various embodiments have been described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise.

Those skilled in the art will appreciate that various other modifications may be made. All these or other variations and modifications are contemplated by the inventors and within the scope of the invention.

What is claimed is:

1. A method, comprising the steps of:
   defining a three-dimensional (3D) geometry of a collimating device which defines an aperture configured to allow a radiation beam passing through;

projecting the collimating device along the radiation beam into a two-dimensional (2D) geometry in a plane;
calculating dosimetric opacity values of the collimating device at locations adjacent to the aperture based on the 3D geometry of the collimating device; and
calculating transport of the radiation beam through the collimating device based on the 2D geometry projected in the plane and using the dosimetric opacity values of the collimating device at the locations adjacent to the aperture.

2. The method of claim 1, wherein the calculating of dosimetric opacity values comprises specifying a number of points of the collimating device at a boundary adjacent to the aperture, calculating dosimetric opacity values at the specified number of points, and performing interpolation between the specified number of points.

3. The method of claim 2, wherein the calculating of dosimetric opacity values at the specified number of points comprises numerical calculation or analytical calculation.

4. The method of claim 1, wherein the calculating of transport of the radiation beam through the collimating device comprises computing a shape and fluence of the radiation beam exiting the collimating device.

5. The method of claim 4, further comprising the step of calculating dose deposition in a subject based on the shape and fluence of the radiation beam exiting the collimating device.

6. The method of claim 1, wherein the collimating device comprises a multileaf collimator (MLC), a stereotactic radiosurgery (SRS) cone, a motorized collimation jaw, or a custom-molded collimation block.

7. The method of claim 6, wherein at least some of the plurality of beam-blocking leaves have a curve leaf tip profile in a side view.

8. The method of claim 1, wherein the aperture of the collimating device has a size and/or shape suitable for stereotactic radiosurgery.

9. A computer product comprising a non-transitory computer-readable medium storing instructions executable by a computer system, the instructions comprising:
defining a three-dimensional (3D) geometry of a collimating device which defines an aperture configured to allow a radiation beam passing through;
projecting the collimating device along the radiation beam into a two-dimensional (2D) geometry in a plane;
calculating dosimetric opacity values of the collimating device at locations adjacent to the aperture based on the 3D geometry of the collimating device; and
calculating transport of the radiation beam through the collimating device based on the 2D geometry projected in the plane and using the dosimetric opacity values of the collimating device at the locations adjacent to the aperture.

10. The computer product of claim 9, wherein the calculating of dosimetric opacity values comprises specifying a number of points of the collimating device at a boundary adjacent to the aperture, calculating dosimetric opacity values at the specified number of points, and performing interpolation between the specified number of points.

11. The computer product of claim 10, wherein the calculating of dosimetric opacity values at the specified number of points comprises numerical or analytical calculation.

12. The computer product of claim 9, wherein the calculating of transport of the radiation beam through the collimating device comprises computing a shape and fluence of the radiation beam exiting the collimating device.

13. The computer product of claim 12, further comprising the step of calculating dose deposition in a subject based on the shape and fluence of the radiation beam exiting the collimating device.

14. A method, comprising the steps of:
providing a collimator which defines at least a portion of an aperture configured to allow a radiation beam passing through;
calculating dosimetric opacity values of the collimator at locations adjacent to the aperture based on a three-dimensional (3D) geometry of the collimator; and
constructing a computational model for calculating radiation transmission through the collimator, wherein the computational model is based on a two-dimensional (2D) geometry of the collimator and includes a function of the dosimetric opacity values of the collimator.

15. The method of claim 14, wherein the calculating of dosimetric opacity values comprises calculating a thickness of the collimator at one of the locations along a ray from a point at a source and a point on a projection plane, and calculating a dosimetric opacity value using the thickness.

16. The method of claim 14, wherein the calculating of dosimetric opacity values comprises determining a number of positions of the collimator in the radiation beam, and calculating dosimetric opacity values of the collimator at the number of the positions.

17. The method of claim 14, wherein the calculating of dosimetric opacity values comprises numerical calculation of dosimetric opacity values at the locations of the collimator and approximation of dosimetric opacity values between the locations.

18. The method of claim 14, wherein the calculating of dosimetric opacity values comprises analytical calculation of dosimetric opacity values at the locations of the collimator and analytical approximation of dosimetric opacity values between the locations.

19. The method of claim 14, further comprising calculating dose deposition in a subject using the calculation of radiation transmission by the computational model.

20. The method of claim 14, wherein the collimator comprises a multileaf collimator (MLC), a stereotactic radiosurgery (SRS) cone, a motorized collimation jaw, or a custom-molded collimation block.

* * * * *